(12) United States Patent
Sasaki et al.

(10) Patent No.: US 8,971,483 B2
(45) Date of Patent: Mar. 3, 2015

(54) X-RAY COMPOSITE APPARATUS

(71) Applicant: Rigaku Corporation, Tokyo (JP)

(72) Inventors: Katsunari Sasaki, Tokyo (JP); Yukihiro Hara, Tokyo (JP); Kiyoshi Akiyama, Tokyo (JP)

(73) Assignee: Rigaku Corporation, Tokyo (JP)

( * ) Notice: Subject to any disclaimer, the term of this patent is extended or adjusted under 35 U.S.C. 154(b) by 133 days.

(21) Appl. No.: 13/796,912

(22) Filed: Mar. 12, 2013

(65) Prior Publication Data

US 2013/0251100 A1    Sep. 26, 2013

(30) Foreign Application Priority Data

Mar. 23, 2012  (JP) ................. 2012-068002

(51) Int. Cl.
  *G01N 23/223*  (2006.01)
  *G01N 23/04*   (2006.01)
  *G01N 23/20*   (2006.01)
  *G01N 23/207*  (2006.01)

(52) U.S. Cl.
  CPC ........... *G01N 23/046* (2013.01); *G01N 23/223* (2013.01); *G01N 23/207* (2013.01)
  USPC .................................. 378/46; 378/16; 378/71

(58) Field of Classification Search
  USPC ...................... 378/4, 16, 46, 70, 71
  See application file for complete search history.

(56) References Cited

U.S. PATENT DOCUMENTS

| | | | |
|---|---|---|---|
| 7,817,779 B2 | 10/2010 | Ando | |
| 2004/0196957 A1 | 10/2004 | Ando | |
| 2006/0182217 A1* | 8/2006 | Harding et al. | 378/44 |
| 2008/0061234 A1* | 3/2008 | Nakamura | 378/44 |
| 2008/0298551 A1 | 12/2008 | Ando | |
| 2011/0200164 A1 | 8/2011 | Blaj | |
| 2014/0072095 A1* | 3/2014 | Feser et al. | 378/4 |

FOREIGN PATENT DOCUMENTS

| | | |
|---|---|---|
| JP | 2-248899 A | 10/1990 |
| JP | 2003-329617 A | 11/2003 |
| JP | 2011-169900 A | 9/2011 |

OTHER PUBLICATIONS

Kitada, "Beauty of Arts and Crafts, and Cultural Properties viewed from Materials Science", Uchida Rokakuho, Mar. 2009, pp. 4-7.

* cited by examiner

*Primary Examiner* — Glen Kao
(74) *Attorney, Agent, or Firm* — Birch, Stewart, Kolasch & Birch, LLP

(57) ABSTRACT

There is provided an X-ray composite apparatus capable of performing, with one unit, X-ray CT and element analysis by fluorescent X-rays. The X-ray composite apparatus 100 includes an X-ray source 110 generating cone beam X-rays, a sample support 150 holding a sample S, collimator parts 130 and 140 capable of narrowing the cone beam X-rays to form parallel X-rays, depending on the intended use, between the X-ray source and the sample support 150, a two-dimensional detector 170 detecting the cone beam X-rays transmitted through the sample S, and a fluorescent X-ray detector 176 detecting fluorescent X-rays radiated from the sample S, and when the apparatus is used for X-ray CT, the apparatus irradiates the sample with the cone beam X-rays, while when the apparatus is used for fluorescent X-ray analysis, the apparatus irradiates the sample S with the parallel X-rays.

9 Claims, 10 Drawing Sheets

X-RAY COMPOSITE APPARATUS

BACKGROUND OF THE INVENTION

1. Field of the Invention

The present invention relates to an X-ray composite apparatus capable of performing, with one unit of apparatus, X-ray CT and structural analysis by X-ray diffraction or element analysis using fluorescent X-rays.

2. Description of the Related Art

X-ray CT is a technology of irradiating a subject with X-rays from the 360° periphery of the subject, recording, with a detector, transmission X-rays partially absorbed by the subject and decayed, and reconstructing an image. Moreover, the X-ray diffraction is a phenomenon in which the X-rays are diffracted by a crystal lattice. Until now, a technology combining the X-ray CT and the X-ray diffraction has been disclosed (See Patent Document 1 and Patent Document 2).

Patent Document 1 proposes an X-ray CT apparatus using X-ray diffraction which achieves CT with high resolution by enlarging a projected image in radiation facilities. The X-ray CT apparatus described in Patent Document 1 irradiates a subject with white X-rays, coverts the white X-rays transmitted through the subject into monochromatic X-rays having a desired X-ray energy value, by asymmetric reflection of a first single crystal and enlarges a projected image at the same time. Then, the reflected projected image is further enlarged by asymmetric reflection of a second single crystal and the subsequent single crystals and unnecessary X-rays of low frequency/high frequency is cut off at the same time, and only monochromatic X-rays of a desired region are enlarged in a final stage.

In addition, Patent Document 2 proposes a non-destructive analysis apparatus capable of obtaining a high contrast image in an object at a time and with ease through the use of the X-ray diffraction. The non-destructive analysis apparatus described in Patent document 2 irradiates an object with monochromatic parallel X-rays, causes refracted X-rays and the like from the object to enter a transmissive crystal analysis body having a predetermined thickness, and photographs a phase contrast image. Then, by introducing the X-ray CT technology into this non-destructive analysis apparatus, new non-destructive analysis image can also be obtained.

Moreover, Patent Document 3 discloses an image system including an X-ray source radiating an X-ray beam, a two-dimensional X-ray detector, a goniometer for relatively locating them at each position, and a computer for processing an input from the two-dimensional detector and outputting information of a sample on the basis of the input from the two-dimensional detector and the relative positions of the X-ray source, the X-ray detector, and the sample. Then, in this image system, angular dispersion X-ray diffraction of the sample can be executed by measuring X-ray diffraction, and a computer tomography mode can be also executed by using the two-dimensional X-ray detector.

[Patent Document 1] Japanese Unexamined Patent Application Publication No. 02-248899
[Patent Document 2] Japanese Unexamined Patent Application Publication No. 2003-329617
[Patent Document 3] Japanese Unexamined Patent Application Publication No. 2011-169900

As described above, Patent Documents 1 and 2 disclose the technology of applying the X-ray diffraction in order to enhance the functions of the X-ray CT. However, the objects of these apparatuses are X-ray CT and are not to perform each of the X-ray CT and the structural analysis by X-ray diffraction. In addition, Patent Document 3 describes the apparatus capable of performing each of the X-ray CT and the structural analysis by the X-ray diffraction, but the apparatus cannot perform element analysis by fluorescent X-rays.

In contrast, in the materials field, there is a demand from users that they want to identify a location of cracks in ceramics used in an electronic component and to also perform structural analysis of the crack location efficiently without putting extra effort. Moreover, when a foreign substance mixed in the material appears on the surface, there are some cases where users want to identify a location of the foreign substance and also to perform element analysis of the foreign substance efficiently.

SUMMARY OF THE INVENTION

The present invention has been made in view of these circumstances and has an object to provide an X-ray composite apparatus capable of performing X-ray CT and element analysis by fluorescent X-rays efficiently with one unit of the apparatus.

(1) In order to achieve the above-described object, an X-ray composite apparatus according to the present invention includes an X-ray source generating cone beam X-rays; a sample support holding a sample to be irradiated with the cone beam X-rays; a collimator part capable of narrowing the cone beam X-rays to form parallel X-rays, depending on the intended use, between the X-ray source and the sample support; a two-dimensional detector detecting the cone beam X-rays transmitted through the sample; and a fluorescent X-ray detector detecting the fluorescent X-rays radiated from the sample, wherein when the apparatus is used for the X-ray CT, the apparatus irradiates the sample with the cone beam X-rays, while when the apparatus is used for the fluorescent X-ray analysis, the apparatus irradiates the sample with the parallel X-rays formed by the collimator part.

As described above, the X-ray composite apparatus of the present invention includes the collimator part for narrowing the X-rays between the X-ray source and the sample support to form the parallel X-rays. Then, when the apparatus is used for the X-ray CT, the X-ray composite apparatus irradiates the sample with the cone beam X-rays without causing the collimator part to function, while when the apparatus is used for the fluorescent X-ray analysis, the X-ray composite apparatus irradiates the sample with the parallel X-rays by causing the collimator part to function. As a result, the X-ray CT and the element analysis by the fluorescent X-rays can be performed by one unit of the X-ray composite apparatus, and a user's effort can be saved as compared with a case where separate apparatuses are used for the respective intended uses.

(2) In addition, the X-ray composite apparatus according to the present invention further includes a two-dimensional detector detecting the cone beam X-rays transmitted through the sample or the X-rays diffracted by the sample, wherein when the apparatus is used for the X-ray diffraction analysis, the apparatus irradiates the sample with the parallel X-rays formed by the collimator part.

As a result, not only the X-ray CT and the element analysis by the fluorescent X-rays but also the structural analysis by the X-ray diffraction can be performed by one unit of the X-ray composite apparatus, and a user's effort such as installation of a sample for respective intended uses or the like can be saved. Furthermore, effects of three units can be obtained with a space for one unit, and space saving can be achieved.

(3) Furthermore, in the X-ray composite apparatus according to the present invention, the collimator part has a hole capable of forming the parallel X-rays when the apparatus is used for the X-ray diffraction analysis or the fluorescent X-ray analysis. As described above, since the size of the hole of the collimator part can be changed depending on the intended use, when the apparatus is used for the X-ray CT, the apparatus can irradiate the sample with the cone beam X-rays without causing the collimator part to function, while when the apparatus is used for the X-ray diffraction or the fluorescent X-ray analysis, the apparatus can irradiate the sample with the substantially parallel X-rays by causing the collimator part to function.

(4) Moreover, in the X-ray composite apparatus according to the present invention, the collimator part is configured by overlapping and installing two slits having the sizes of the holes capable of being adjusted. The size of the slit hole can be adjusted easily depending on the intended uses of the X-ray CT and others.

(5) Additionally, the X-ray composite apparatus according to the present invention further includes a CT filter that is capable of advancing to or retreating from an irradiation path of the cone beam X-rays and that blocks an X-ray component having a wavelength of a predetermined value or more, wherein the CT filter is mainly formed of aluminum or beryllium. As described above, the CT filter blocks the X-ray component having a wavelength of a predetermined value or more when it is used for X-ray CT. As a result, an irradiation amount of the X-rays absorbed by a subject can be reduced, and an influence by the X-ray irradiation can be reduced. Furthermore, by omitting scattered radiation caused by unnecessary irradiation, contrast of the CT image can be enhanced. Note that the CT filter functions as a CT absorber for selectively decaying the X-rays having an energy of a predetermined value or less. Moreover, blocking of the X-ray component having a wavelength of a predetermined value or more substantially means that most of the X-ray component having the wavelength of a predetermined value or more is blocked.

Being mainly formed of aluminum or beryllium means that aluminum or beryllium is contained to the extent that the function of the CT filter for blocking the X-rays having the wavelength of a predetermined value or more is achieved. Note that, when only omission of the scattered radiation caused by unnecessary irradiation is intended, a CT filter formed of yttrium, molybdenum, or a material containing yttrium and molybdenum may be used.

(6) Furthermore, the X-ray composite apparatus according to the present invention further includes a diffraction filter that is capable of advancing to or retreating from an irradiation path of the cone beam X-rays and that blocks the X-rays having a specific wavelength, wherein the diffraction filter is mainly formed of zirconium, hafnium, rhodium or nickel. As described above, the diffraction filter blocks the X-rays having a specific wavelength when it is used for X-ray diffraction analysis. As a result, generation of an unnecessary diffraction image can be prevented by, for example, keeping Kβ rays low. Being mainly formed of zirconium, hafnium, rhodium or nickel means that zirconium, hafnium, rhodium or nickel is contained to the extent that the function of the diffraction filter for blocking the X-rays having a specific wavelength is achieved.

(7) Moreover, the X-ray composite apparatus according to the present invention further includes a filter switching part switching between the CT filter and a diffraction filter on an irradiation path of the cone beam X-rays. As a result, switching of the filter depending on the intended use becomes facilitated.

(8) Moreover, in the X-ray composite apparatus according to the present invention, an applied voltage can be adjusted so that, when the X-ray CT is to be performed, the X-ray source generates X-rays having 150 kV or less, while when the structural analysis by the X-ray diffraction or the fluorescent X-ray analysis is to be performed, the X-ray source generates X-rays having 100 kV or less.

For example, the X-ray composite apparatus of the present invention has an operation part receiving an operation for adjusting a tube voltage of the X-ray source and may be configured such that the tube voltage can be adjusted by a user's operation. Additionally, the X-ray composite apparatus may be configured to automatically switch the tube voltage depending on the X-ray CT, the X-ray diffraction analysis and the like.

(9) Moreover, the X-ray composite apparatus according to the present invention further includes a moving mechanism making it possible to move the sample from a sample position for the X-ray CT to a sample position for the X-ray diffraction analysis or the fluorescent X-ray analysis, by moving the sample support.

As a result, the sample can be moved to the position where a part of the sample to be further analyzed is specified from a result obtained by the X-ray CT of the sample and the part can be subjected to the X-ray diffraction analysis or the fluorescent X-ray analysis without removing the sample from the sample support. The sample position for the X-ray CT is a position of the sample where irradiation with the cone beam X-rays can be performed, and the sample position for the X-ray diffraction analysis or the fluorescent X-ray analysis is a position of the sample where the parallel X-rays can be applied at least to apart thereof. The moving mechanism can move the sample support over a range which can cover these positions.

According to the present invention, the X-ray CT and the fluorescent X-ray analysis can be performed efficiently with one unit of the X-ray composite apparatus, and a user's effort can be saved as compared with the case where separate apparatuses are used in accordance with the respective intended uses. Moreover, a work of two or three units can be accomplished in a space for one unit, and space saving can be achieved.

DETAILED DESCRIPTION OF THE INVENTION

Figure 1:
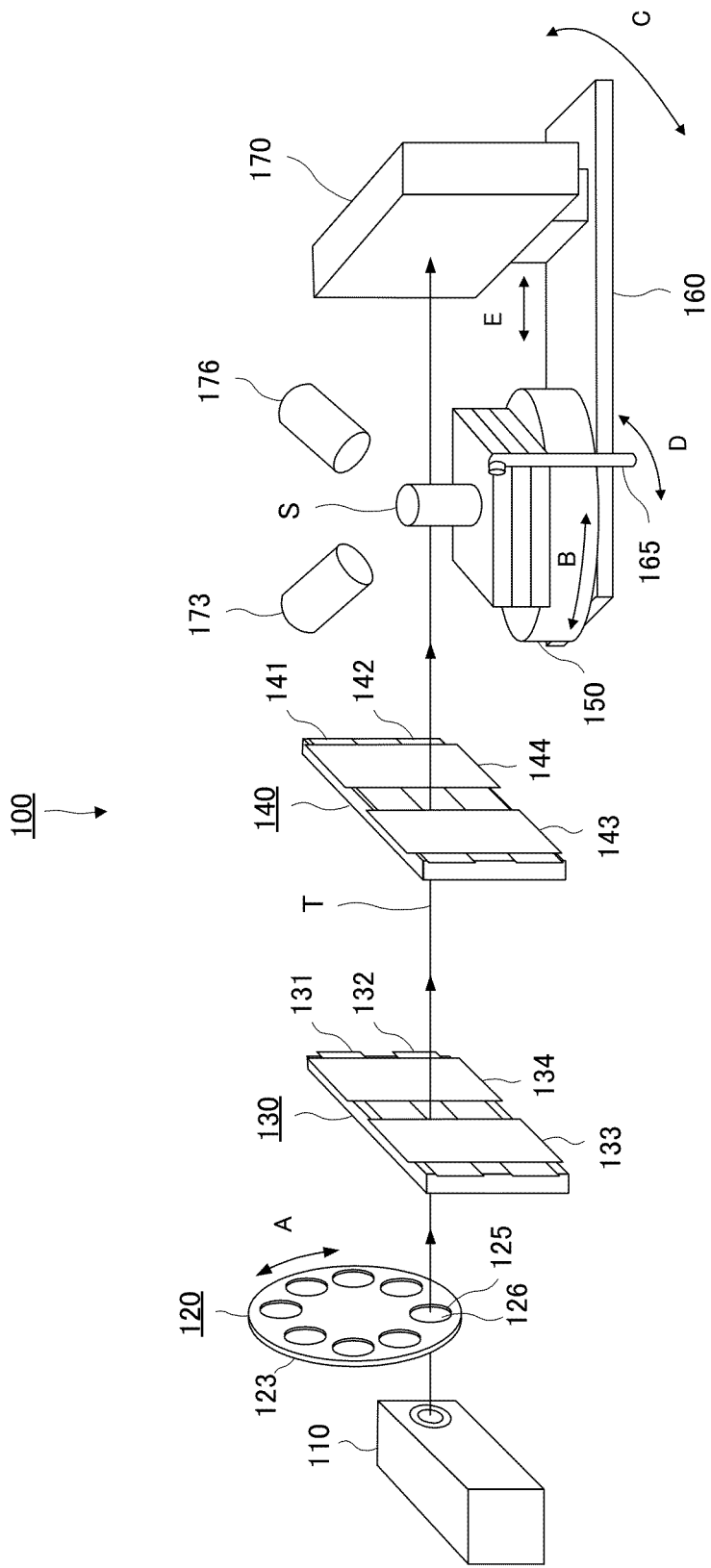
FIG. 1 is a perspective view illustrating an example of a configuration of an X-ray composite apparatus according to the present invention (First Embodiment).

First, embodiments of the present invention will be described by referring to the attached drawings. In order to facilitate understanding of the explanation, the same reference numerals are given to the same constituent elements in each drawing and duplicated explanation will be omitted.

First Embodiment

FIG. 1 is a perspective view illustrating an example of a configuration of an X-ray composite apparatus 100. As illustrated in FIG. 1, the X-ray composite apparatus 100 is composed of X-ray source 110, a revolver-type filter switching part 120, electric slits 130 and 140, a sample support 150, a 2θ mechanism 160, a beam stopper 165, a two-dimensional detector 170, a camera 173, and a fluorescent X-ray detector 176. In FIG. 1, an irradiation direction of an irradiation path T of X-rays is indicated by an arrow.

The X-ray source 110 generates X-rays by means of application of a predetermined tube voltage. As a target, molybdenum, tungsten, silver, copper or the like is used, for example. The voltage to be applied can be adjusted by user's operation. An applied voltage of approximately 150 kV is suitable in the case of performing X-ray CT and an applied voltage of approximately 100 kV is suitable in the case of performing X-ray diffraction analysis.

The revolver-type filter switching part 120 includes a revolver part 123 and a plurality of filters 126. The revolver part 123 holds the filters 126 in filter installation holes 125. The revolver-type filter switching part 120 is capable of replacing the filter on the X-ray irradiation path by rotating the revolver part 123 in an A direction in FIG. 1 upon receiving the user's operation. By means of the filter 126 set on the X-ray irradiation path as described above, unnecessary X-rays are blocked. Moreover, when it is not necessary to pass the X-rays through the filter 126, the X-rays can be caused to transmit therethrough by setting the filter installation hole 125 not holding the filter 126, on the X-ray irradiation path. Note that the filter switching part does not necessarily have to be a revolver type but can be anything as long as the filter can be replaced on the X-ray irradiation path, depending on the intended use. For example, the filter switching part may be of a type capable of performing filter replacement by insertion of a filter by a user.

There are two types of the filter 126, that is, a CT filter 126a and a diffraction filter 126b. As the CT filter 126a, an aluminum filter having a thickness of approximately 1 to 2 mm or a beryllium filter having a thickness of approximately 3 to 10 mm is used, for example. In addition, as the diffraction filter, a Kβ filter formed of zirconium, hafnium, rhodium, nickel or the like can be used, for example. The revolver-type filter switching part 120 can hold the plurality of filters and switch the filters depending on the intended use. For example, for the X-ray generated using molybdenum as a target, a zirconium filter can be set in accordance with that.

The two electric slits 130 and 140 (collimator parts) are provided on the irradiation path of X-rays with which the X-ray source 110 performs irradiation. The electric slit 130 has upper and lower slits 131 and 132 that move electrically in the vertical direction upon receiving the user's operation and has left and right slits 133 and 144 that move in the right and left directions. Furthermore, similarly, the electric slit 140 has upper and lower slits 131 and 132 and has left and right slits 133 and 144.

The electric slits 130 and 140 are capable of opening/closing the upper and lower slits and the right and left slits upon receiving the user's operation, respectively. As a result, the electric slits 130 and 140 are capable of adjusting a gap between the slits from four directions, and narrowing the X-rays between the X-ray source 110 and the sample support 150 to thereby form parallel X-rays. For example, when the X-ray composite apparatus 100 is to be used for X-ray CT, the slit is opened wide and a sample is irradiated with cone beam X-rays, while when it is used for X-ray diffraction analysis or fluorescent X-ray analysis, the slit is made narrower and the sample can be irradiated with substantially parallel X-rays. As a result, the X-ray CT, X-ray diffraction analysis, and fluorescent X-ray analysis can be performed with one unit of the X-ray composite apparatus 100, and a user's effort can be saved as compared with a case where separate apparatuses are used for the respective intended uses. Moreover, effects of three units can be obtained with a space for one unit, and space saving can be achieved. Note that, instead of opening/closing of the slits by the electric slits 130 and 140, a pinhole slit may be electrically advanced/retreated with respect to the irradiation path or may be attached/detached by a user.

The sample support 150 is a support for fixing a sample S on the X-ray irradiation path where the sample to be irradiated with X-rays is held. The sample support 150 is connected to a moving mechanism (not shown) and is capable of parallel movement in a xyz direction and φ-axis rotation (rotary movement in a B direction in the figure) by the user's operation, whereby the position of the sample S can be adjusted (positioning, centering). Furthermore, in the case of the X-ray CT, the sample support 150 makes φ-axis rotation by 360° in synchronization with the imaging. Moreover, the sample support 150 is installed on a 2θ mechanism 160 and is designed to rotate along with movement of the two-dimensional detector 170 if necessary in the X-ray diffraction analysis.

By using the above-described moving mechanism, a part of the sample S to be further analyzed is specified from a result obtained by X-ray CT of the sample S, and the sample S can be moved to a position where the part can be subjected to X-ray diffraction analysis or fluorescent X-ray analysis without removing the sample S from the sample support 150. Therefore, by means of the moving mechanism, the sample support 150 can be freely moved from the position where the sample S can be irradiated with the cone beam X-rays to the position where the parallel X-rays can be applied at least to a part thereof. For example, when a foreign region is found inside the sample S in a CT image, the sample S is moved in the XYZ direction by using the above-described moving mechanism so that the parallel X-rays are applied to the region, and X-ray diffraction analysis or fluorescent X-ray analysis is performed. Then, the sample is rotated by 90° on the surface of the sample support 150, and the sample S can be analyzed at that position. As described above, X-ray diffraction analysis or fluorescent X-ray analysis can be performed continuously subsequent to the X-ray CT.

The 2θ mechanism 160 has the sample support 150 and the two-dimensional detector 170 installed thereon, and in X-ray diffraction analysis, the sample S and the two-dimensional detector are rotated and moved in a C direction while a Brag angle is maintained. The beam stopper 165 is for stopping a direct beam in X-ray diffraction analysis or fluorescent X-ray analysis. The beam stopper 165 can be installed on the direct beam (on a straight line of an incident X-ray path) of the X-rays between the sample and the two-dimensional detector 170. The beam stopper 165 moves onto the direct beam when X-ray diffraction analysis or fluorescent X-ray analysis is to be performed in accordance with the user's operation and retreats from an irradiation range of the X-rays so as not to obstruct X-ray CT when the X-ray CT is to be performed.

The two-dimensional detector 170 is a combination detector functioning not only as a CT detector for detecting transmission X-rays of the sample S, but also as a diffraction detector for detecting diffraction X-rays by the sample S. The two-dimensional detector 170 is provided on the side opposite to the X-ray source 110 with respect to the sample S. A detection surface is perpendicular to the path of the incident X-rays. The two-dimensional detector 170 is movable in an E direction by the user's operation and is capable of adjusting a distance to the sample S and capable of enlargement and reduction of the CT image. As described above, the two dimensional detector 170 is coupled to the 2θ mechanism 160, and when X-ray diffraction analysis is to be performed, the two dimensional detector moves with the sample S in conjunction with them.

The camera 173 is an optical CCD camera and is provided at a position where the position of the sample S can be confirmed. The camera 173 is directed toward the sample S and picks up an image of the sample S. The image of the sample photographed by the camera 173 is displayed on a monitor (not shown). A display magnification is variable from 20 to 300 times. The user can make fine adjustment of the sample S while watching the monitor. The fluorescent X-ray detector 176 is an energy-dispersive X-ray detector and uses a semiconductor detector or the like having energy resolution for X-rays which are being counted. The fluorescent X-ray detector 176 detects fluorescent X-rays radiated from the sample S. The fluorescent X-ray detector 176 is installed at a position where the radiated fluorescent X-rays can be detected easily.

Figure 2:
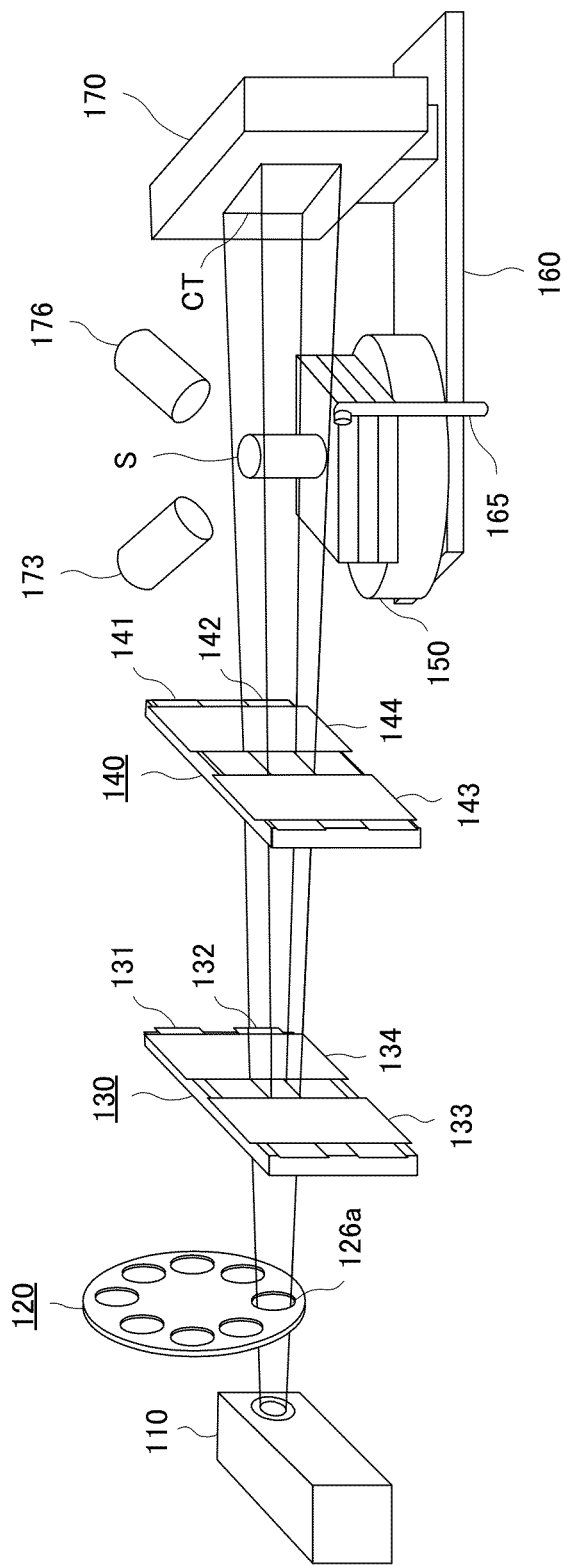
FIG. 2 is a diagram illustrating a mode of X-ray CT using the X-ray composite apparatus according to the present invention.

A method of using the X-ray composite apparatus 100 configured as above will be described below. FIG. 2 is a diagram illustrating a mode of X-ray CT performed using the X-ray composite apparatus 100. First, the sample S is fixed to the sample support 150. The size of the sample S is preferably square of 30 mm×30 mm or less. The sample S suitable for the X-ray composite apparatus 100 includes, for example, electronic components, bones and the like. As to the electronic components, while detecting internal cracks or internal foreign substances, it is possible to perform structural analysis or element analysis at the periphery thereof. Moreover, it is possible to measure orientation of a bone while observing a transparent image of the bone.

After the sample S is fixed, the filter suitable for X-ray CT is set. In the case of performing X-ray CT, the CT filter 126a is set on the revolver-type filter switching part 120, and the CT filter 126a is moved onto the X-ray irradiation path. The CT filter 126a blocks the X-ray component having a wavelength of a predetermined value or more. As the CT filter 126a, a filter of aluminum having a thickness of approximately 1 to 2 mm or a filter of beryllium having a thickness of approximately 3 to 10 mm is suitably used.

Next, the upper and lower slits 131, 132, 141, and 142 and the left and right slits 133, 134, 143, and 144 of the electric slits 130 and 140 are opened, and an interval between each slit is adjusted so that the sample S can be irradiated with the cone beam. In this case, the position of the sample support 150 is adjusted to a position where an image can be sufficiently picked up by the two-dimensional detector 170 when the sample S makes a rotation. In contrast, an interval between the two-dimensional detector 170 and the sample S is adjusted, and the beam stopper 165 is retreated. Then, X-rays are generated with a predetermined tube voltage and the sample S is irradiated with the X-rays, and the transmission X-rays, that is, a transparent image CT is detected by the two-dimensional detector 170. As described above, X-ray CT is performed.

Figure 3:
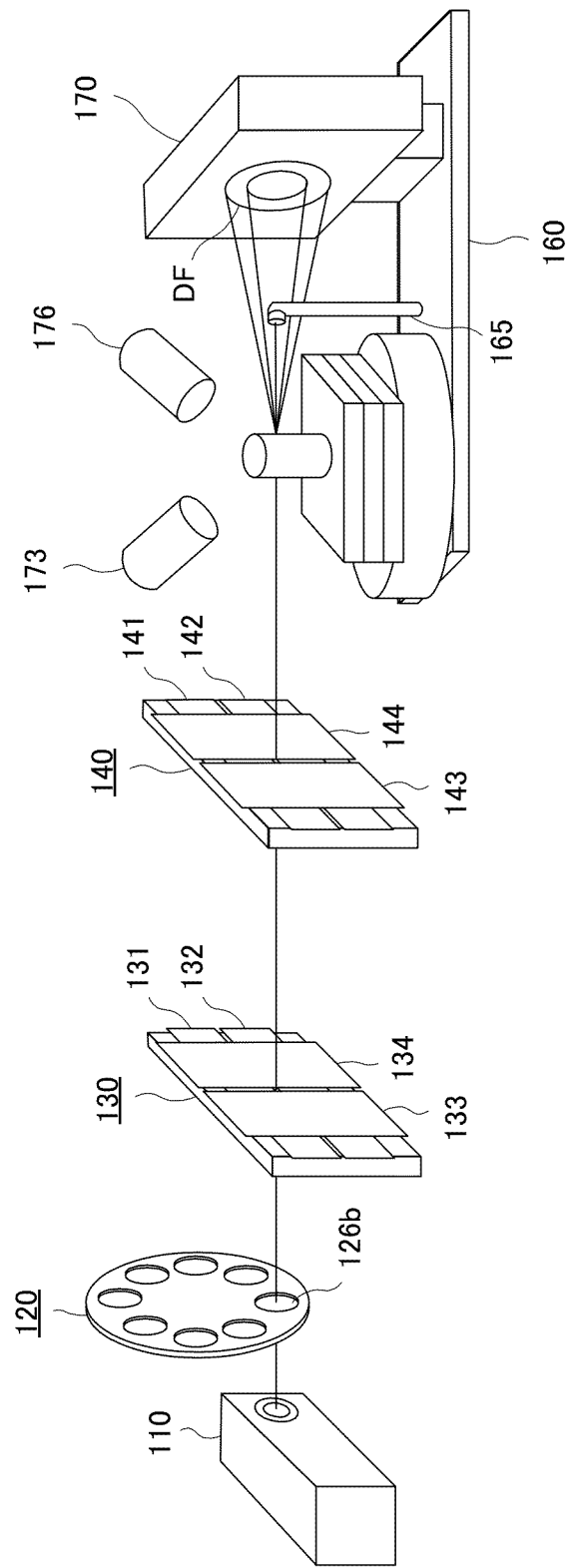
FIG. 3 is a diagram illustrating a mode of X-ray diffraction analysis using the X-ray composite apparatus according to the present invention.

Then, a case where X-ray diffraction analysis is performed will be described. FIG. 3 is a diagram illustrating a mode of X-ray diffraction analysis performed using the X-ray composite apparatus 100. First, the sample S is fixed to the sample support 150. After the sample S is fixed, a filter suitable for X-ray diffraction analysis is set. In this case, a Kβ filter is suitably used as the diffraction filter 126b to be installed in the revolver-type filter switching part 120. As the Kβ filter, a filter of, for example, zirconium, hafnium, rhodium or nickel can be included.

Subsequently, the upper and lower slits 131, 132, 141, and 142 of the electric slits 130 and 140 are narrowed and adjusted so that the sample S can be irradiated with parallel X-rays. Furthermore, the position of the sample support 150 is adjusted to a position where incident X-rays are applied to the sample S. In contrast, the interval between the two-dimensional detector 170 and the sample S is adjusted so that desired diffraction rays can be detected. The beam stopper 165 is installed on the irradiation path of the direct beam. Then, X-rays are generated with a predetermined tube voltage and the sample S is irradiated with the X-rays, and the diffraction X-rays DF are detected by the two-dimensional detector 170. As described above, X-ray diffraction analysis is performed.

Figure 4:
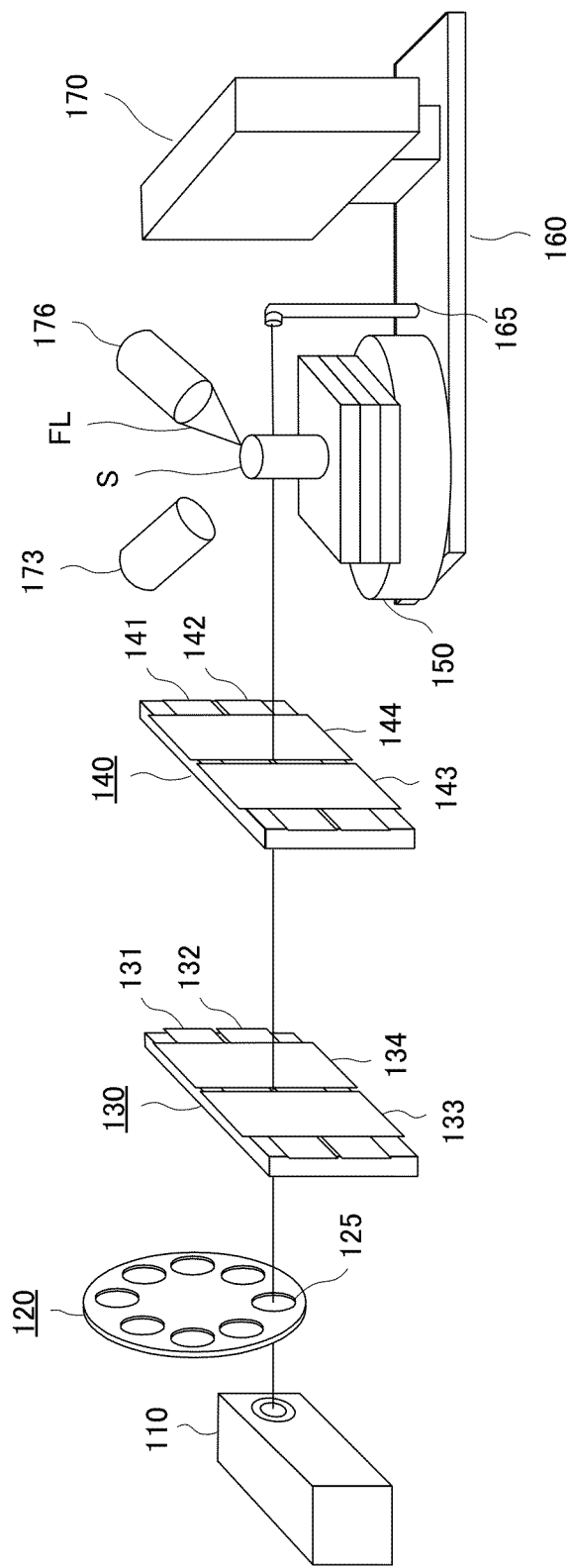
FIG. 4 is a diagram illustrating a mode of fluorescent X-ray analysis using the X-ray composite apparatus according to the present invention.

Then, a case where fluorescent X-ray analysis is performed will be described. FIG. 4 is a diagram illustrating a mode of fluorescent X-ray analysis performed by using the X-ray composite apparatus 100. In this case, a filter does not particularly have to be set.

First, the upper and lower slits 131, 132, 141, and 142 and the left and right slits 133, 134, 143, and 144 of the electric slits 130 and 140 are narrowed and adjusted so that the sample S can be irradiated with parallel X-rays. Furthermore, the position of the sample support 150 is adjusted to a position where incident X-rays are applied to the sample S. In contrast, the interval between the fluorescent X-ray detector 176 and the sample S is adjusted so that fluorescent X-rays can be detected. The beam stopper 165 is installed on the irradiation path of the direct beam. Then, X-rays are generated with a predetermined tube voltage and the sample S is irradiated with the X-rays, and the fluorescent X-rays FL are detected by the fluorescent X-ray detector 176. As described above, fluorescent X-ray analysis is performed.

Second Embodiment

Figure 5:
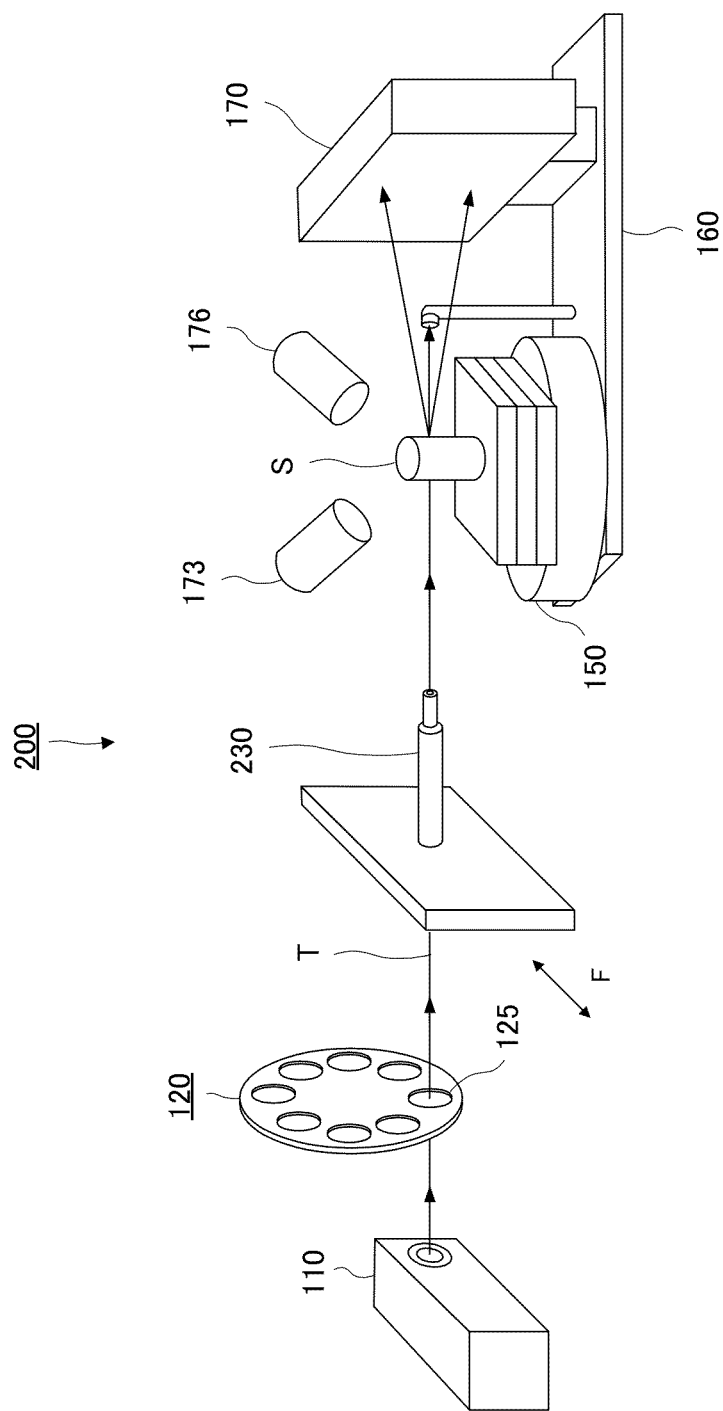
FIG. 5 is a perspective view illustrating an example of a configuration of an X-ray composite apparatus according to the present invention (Second Embodiment).

In the above-described embodiment, the electric slits 130 and 140 are used as a collimator part which switches between the cone beam and the parallel X-rays, but a collimator 230 capable of advancing/retreating on the X-ray irradiation path may be also used. FIG. 5 is a perspective view illustrating an X-ray composite apparatus 200 using the collimator 230 instead of the electric slits 130 and 140. In FIG. 5, an irradiation direction of the irradiation path T of the X-rays is indicated by an arrow.

As illustrated in FIG. 5, the X-ray composite apparatus 200 includes the collimator 230 instead of the electric slits 130 and 140. The collimator 230 is capable of forming parallel X-rays on the irradiation path of the cone beam X-rays. The collimator 230 is capable of advancing/retreating in an F direction in FIG. 5 by, for example, the user's operation.

As described above, by advancing/retreating the collimator 230, an effort of adjustment or the like of opening/closing the slits can be saved. As described above, the collimator part has only to have a function of forming parallel X-rays by narrowing the X-rays when it is used in X-ray diffraction or fluorescent X-ray analysis. Therefore, the collimator 230 that is electrically operated and capable of advancing/retreating is used in the above-described example, but it may be a collimator that can be attached/detached by a user.

Procedures of Application Example

An application example using the X-ray composite apparatus 100 will be described. By using the X-ray composite apparatus 100 illustrated in FIG. 1 as below, component information, for the sample, identified from an X-ray diffraction measurement result or a fluorescent X-ray analysis result can be mapped on a CT image.

First, the upper and lower slits 131, 132, 141, and 142 and the left and right slits 133, 134, 143, and 144 are opened, and an interval between each slit is adjusted so that the sample S can be irradiated with the cone beam X-rays. Then, the entire sample S is subjected to cone beam X-ray CT. By using the cone beam, three-dimensional information of the entire sample can be grasped.

After the X-ray CT is finished, CT software is executed on a PC, X-ray CT data is used on the CT software to observe an X-ray CT image, and a location requiring component analysis is specified on the CT software. For example, a region of interest on the CT image is clicked by a mouse.

The sample S is moved so that the position specified on the CT software can be subjected to X-ray diffraction analysis or fluorescent X-ray analysis, and an optical system is set. Moreover, the slit, the filter and the like are changed to shapes suitable for X-ray diffraction analysis. When measurement preparation is completed, X-ray irradiation is performed, and X-ray diffraction measurement is executed. As a result, orientation of the specified location and the like can be detected. In the X-ray composite apparatus 100, since three functions are provided in one unit, an effort of replacing and positioning the sample S can be saved as compared with prior-art methods.

Next, the slits, the filters and the like are changed to the shapes suitable for fluorescent X-ray analysis, X-ray irradiation is performed, and fluorescent X-ray analysis is performed. As a result, an element of the specified location can be detected. Component information identified from the X-ray diffraction measurement result and the fluorescent X-ray analysis result performed as above is mapped on the CT software. For example, through the use of different colors for each component on a 3D image of CT, the information can be synthesized. As described above, it can be known how parts having three-dimensionally different densities are distributed.

First Application Example

The above-described method is suitable for three-dimensional nondestructive tests. In the case of industrial materials, foreign substances might be mixed in during, for example, a manufacturing stage, and it is important for quality control to discover foreign substances and to identify the position and component of the foreign substances.

Figure 6:
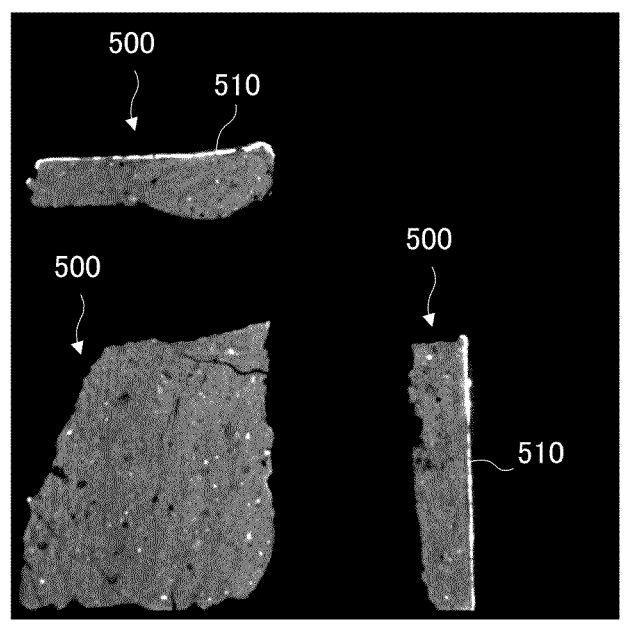
FIG. 6 is a diagram illustrating respective CT cross-sectional images of a front, a plane and a side of a sample.

FIG. 6 is a diagram illustrating CT cross-sectional images of each of a front, a plane and a side of a sample (wall material 500). As illustrated in FIG. 6, an image with light-to-dark contrast in accordance with the density can be obtained in X-ray CT images and three-dimensional positional relationships can be measured for the density. According to FIG. 6, there can be observed a state where a material 510 with high density is distributed so as to cover the surface.

Figure 7:
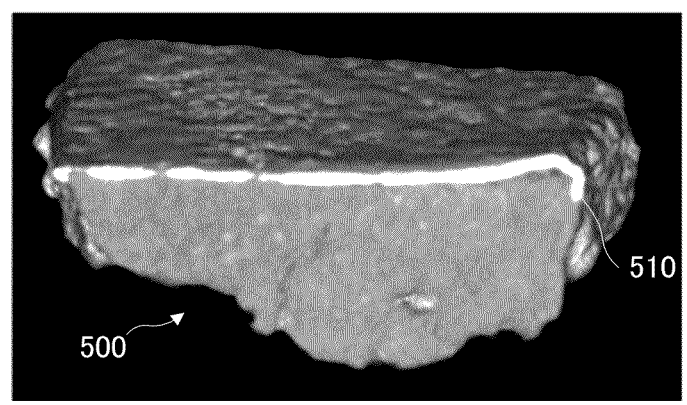
FIG. 7 is a diagram illustrating a 3D image of the sample.

FIG. 7 is a diagram illustrating a 3D image of the sample (wall material 500). In 3D images, three-dimensional distribution of a specific material can be observed. It can be ascertained from the 3D image that the material 510 with high density confirmed on the CT cross-sectional image does not cover the surface uniformly but is distributed.

In this case, furthermore, it is effective to perform X-ray diffraction analysis and fluorescent X-ray analysis for a specific region in a CT image in order to identify, for example, the component of the material covering the surface. In the above-described example, a part of the material 510 with high density, covering the surface is analyzed.

As described above, the X-ray composite apparatus 100 combines, in one unit, the X-ray CT function, the X-ray diffraction analysis function, and the fluorescent X-ray analysis function, and thus three-dimensional position information, components, composition information can be easily mapped by using measurement results. Note that the use of a transmission image without using X-ray CT can be an option, but in the case of the transmission image, it cannot be determined whether the light-to-dark contrast of the image is caused by density distribution or spatial thickness. In contrast to this, the X-ray composite apparatus 100 would be able to reliably detect density distribution.

Second Application Example

By using the X-ray composite apparatus 100, an internal structure can be also estimated easily. For example, it is possible to specify a specific position on a 3D image, to identify a material and a structure at the position by using X-ray diffraction analysis or fluorescent X-ray analysis, and to display, in a 3D image, the location having the same material and structure as that at the position.

Figure 8:
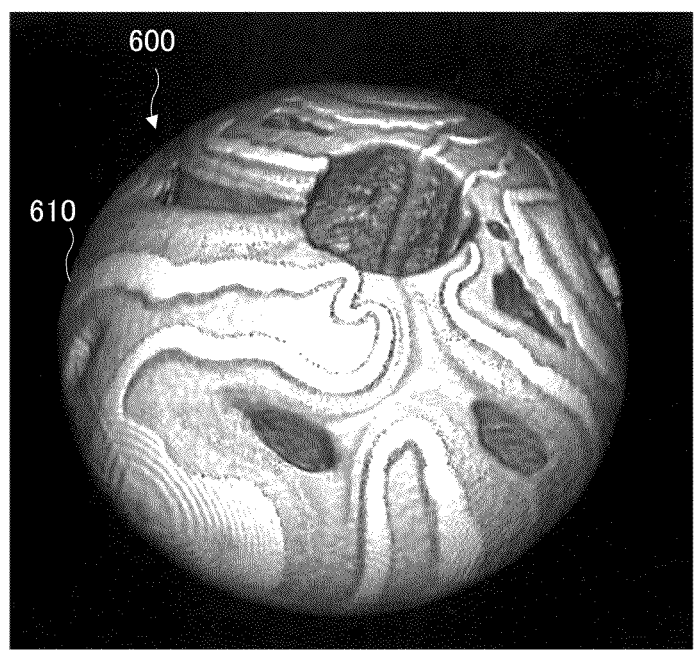
FIG. 8 is a photograph illustrating the sample.
Figure 9:
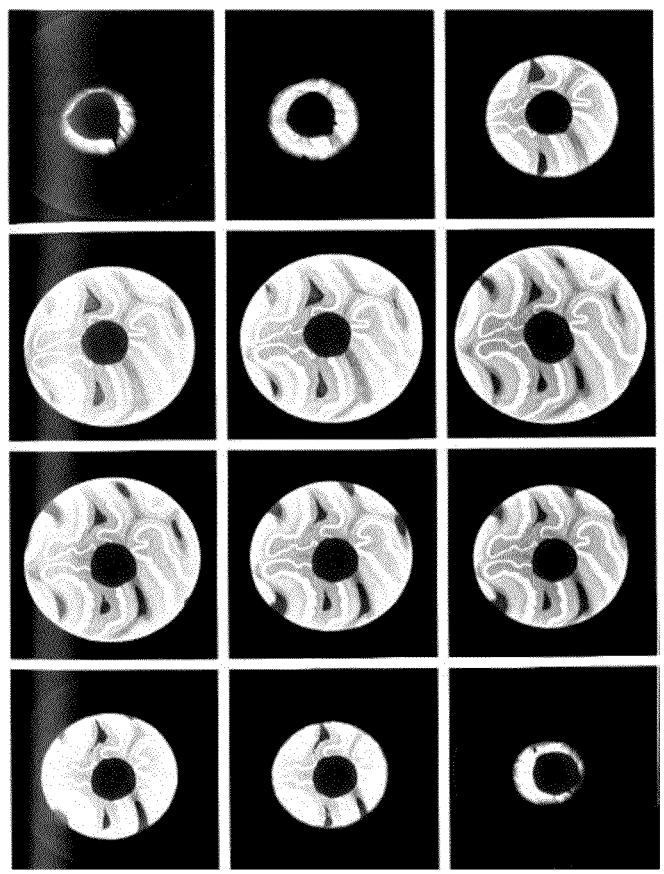
FIG. 9 are respective cross-sectional views illustrating a sample taken in X-ray CT.

FIG. 8 is a photo illustrating a sample (a bead 600 of a hair accessory). When the bead 600 is subjected to X-ray CT by cone beam X-rays as illustrated in FIG. 8, density distribution of the inside can be measured. FIG. 9 are respective cross-sectional views illustrating a sample (the bead 600) taken in X-ray CT. In FIG. 9, views of each of the cross-sections from the front to the depth are illustrated in order from left to right and from the upper to the lower row, for each row.

Figure 10:
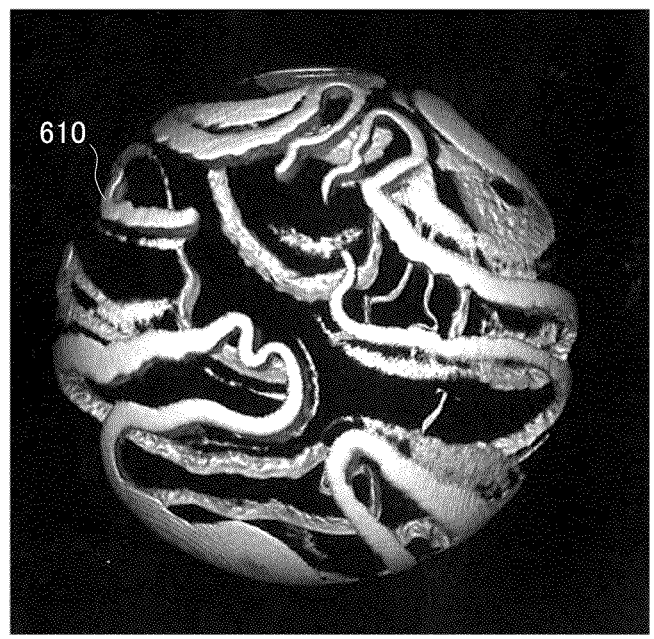
FIG. 10 is a diagram illustrating a 3D image which takes out only a structural part having low density in the sample.

In the X-ray composite apparatus 100, on the surface of the bead 600 displayed as a 3D image, when, for example, a structural part 610 having low density is specified, only the specified structural part 610 having low density, also including the internal structure can be taken out and be displayed in that state. FIG. 10 is a diagram illustrating a 3D image in which only a structural part with low density in the sample is taken out. Note that the examples illustrated in FIG. 8 to 10 are analyzed and displayed by using another apparatus (cited from "Beauty of Arts and Crafts, and Cultural Properties viewed from Materials Science" by Masahiro Kitada, published by Uchida Rokakuho, pp. 4 to 7), but by using the X-ray composite apparatus 100, the equivalent analysis can be performed easily.

What is claimed is:
1. An X-ray composite apparatus comprising:
an X-ray source generating cone beam X-rays;
a sample support holding a sample to be irradiated with the cone beam X-rays;
a collimator part capable of narrowing the cone beam X-rays to form parallel X-rays, depending on the intended use, between the X-ray source and the sample support;
a two-dimensional detector detecting the cone beam X-rays transmitted through the sample; and
a fluorescent X-ray detector detecting the fluorescent X-rays radiated from the sample, wherein
when the apparatus is used for X-ray computed tomography (CT), the apparatus irradiates the sample with the cone beam X-rays, while when the apparatus is used for fluorescent X-ray analysis, the apparatus irradiates the sample with the parallel X-rays formed by the collimator part.
2. The X-ray composite apparatus according to claim 1, further comprising:

a two-dimensional detector detecting the cone beam X-rays transmitted through the sample or X-rays diffracted by the sample, wherein when the apparatus is used for X-ray diffraction analysis, the apparatus irradiates the sample with the parallel X-rays formed by the collimator part.

3. The X-ray composite apparatus according to claim 1, wherein the collimator part has a hole capable of forming the parallel X-rays when the apparatus is used for X-ray diffraction analysis or the fluorescent X-ray analysis.

4. The X-ray composite apparatus according to claim 3, wherein the collimator part is configured by overlapping and installing two slits having sizes of holes capable of being adjusted.

5. The X-ray composite apparatus according to claim 1, further comprising:

a CT filter that is capable of advancing to or retreating from an irradiation path of the cone beam X-rays and that blocks an X-ray component having a wavelength of a predetermined value or more, wherein the CT filter is mainly formed of aluminum or beryllium.

6. The X-ray composite apparatus according to claim 1, further comprising:

a diffraction filter that is capable of advancing to or retreating from an irradiation path of the cone beam X-rays and that blocks X-rays having a specific wavelength, wherein the diffraction filter is mainly formed of zirconium, hafnium, rhodium or nickel.

7. The X-ray composite apparatus according to claim 1, further comprising:

a filter switching part switching between a CT filter and a diffraction filter on an irradiation path of the cone beam X-rays.

8. The X-ray composite apparatus according to claim 1, wherein an applied voltage can be adjusted so that, when the X-ray CT is to be performed, the X-ray source generates X-rays having 150 kV or less, while when structural analysis by X-ray diffraction or the fluorescent X-ray analysis is to be performed, the X-ray source generates X-rays having 100 kV or less.

9. The X-ray composite apparatus according to claim 1, further comprising:

a moving mechanism making it possible to move the sample from a sample position for the X-ray CT to a sample position for X-ray diffraction analysis or the fluorescent X-ray analysis, by moving the sample support.

* * * * *